United States Patent
El Tayar et al.

(10) Patent No.: US 6,482,925 B1
(45) Date of Patent: Nov. 19, 2002

(54) MUTANTS OF THE LAG-3 PROTEINS AND NUCLEOTIDES ENCODING LAG-3 MUTANTS

(75) Inventors: Nabil El Tayar, Milton, MA (US); Bertrand Huard, L'Haye les Roses (FR); Renato Mastrangeli, Rome (IT); Frederic Triebel, Versailles (FR)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/319,014

(22) PCT Filed: Nov. 25, 1997

(86) PCT No.: PCT/FR97/02126

§ 371 (c)(1), (2), (4) Date: Jan. 6, 2000

(87) PCT Pub. No.: WO98/23741

PCT Pub. Date: Jun. 4, 1998

(30) Foreign Application Priority Data

Nov. 28, 1996 (FR) .............................. 96 14608

(51) Int. Cl.[7] .......................... C07K 1/00; C07K 14/00; C07K 17/00
(52) U.S. Cl. ............... 530/351; 424/278.1; 530/388.22; 536/23.1; 536/23.4; 536/23.5
(58) Field of Search ................. 424/278.1; 530/351, 530/388.22; 536/23.1, 23.4, 23.5

(56) References Cited

PUBLICATIONS

Triebel, F. et al., "LAG–3, A novel lymphocyte activation gene closely related to CD4.", J.Exp.Med., vol. 171, pp. 1393–1405 (1990).

Baixeras, E. et al., "Characterization of the lymphocyte activation gene 3–encoded protein. A new ligand for human leukocyte antigen class II antigens.", J.Exp.Med., vol. 176, pp. 327–337 (1992).

Huard, B. et al., "CD4/major histocompatibility complex class II interaction analyzed with CD4–and lymphocyte activation gene–3 (LAG–3)–Ig fusion proteins.", Eur. J. Immunol., vol. 25, pp. 2718–2721 (1995).

Fleury, S. et al., "Mutational analysis of the interaction between CD4 and class II MHC: class II antigens contact CD4 on a surface opposite the gp120–binding site.", Cell, vol. 66, pp. 1037–1049 (1991).

Huard, B. et al., "Characterization of the major histocompatibility complex class II binding site on LAG–3 protein.", Proc. Natl. Acad. Sci., vol. 94, pp. 5744–5749 (1997).

Huard, B. et al., "The lymphocyte activation gene product LAG–3 is a ligand for class II antigen.", Abstract from the Proceedings of the International Congress of Immunology, p. 281 (1992).

*Primary Examiner*—Patrick J. Nolan
*Assistant Examiner*—Gerald R. Ewoldt
(74) *Attorney, Agent, or Firm*—Browdy and Neimark

(57) ABSTRACT

The invention concerns a purified polypeptide corresponding to a mutated form of the soluble LAG-3 protein or of one of its fragments comprising the extra-cellular domain D1 and D2.

6 Claims, 7 Drawing Sheets

```
1       300       310       320       330       340       350
2    CTCCAGCCAGGGGCTGAGGTCCCGGTGGTGTGGGCCCAGGAGGGGGCTCCTGCCCAGCTC
3     L  Q  P  G  A  E  V  P  V  V  W  A  Q  E  G  A  P  A  Q  L
4     1                          10                            20

1       360       370       380       390       400       410
2    CCCTGCAGCCCCACAATCCCCCTCCAGGATCTCAGCCTTCTGCGAAGAGCAGGGGTCACT
3     P  C  S  P  T  I  P  L  Q  D  L  S  L  L  R  R  A  G  V  T
4                               30    ================>         40
                                        Amorce 1       420      SfanI 440       450       460       470
2    TGGCAGCATCAGCCAGACAGTGGCCCGCCCGCTGCCGCCCCGGCCATCCCCTGGCCCC
3     W  Q  H  Q  P  D  S  G  P  P  A  A  A  P  G  H  P  L  A  P
4                               50                             60

1       480       490       500       510  ***  ******  530EspI
2    GGCCCTCACCCGGCGGCGCCCTCCTCCTGGGGGCCCAGGCCCCGCCGCTACACGGTGCTG
3     G  P  H  P  A  A  P  S  S  W  G  P  R  P  R  R  Y  T  V  L
4                                      <===========================
                                              Amorce 1       540       550       560       570       580       590
2    AGCGTGGGTCCCGGAGGCCTGCGCAGCGGGAGGCTGCCCCTGCAGCCCCGCGTCCAGCTG
3     S  V  G  P  G  G  L  R  S  G  R  L  P  L  Q  P  R  V  Q  L
4    ======                          90                          100

1       600       610       620       630       640       650
2    GATGAGCGCGGCCGGCAGCGCGGGGACTTCTCGCTATGGCTGCGCCCAGCCCGGCGCGCG
3     D  E  R  G  R  Q  R  G  D  F  S  L  W  L  R  P  A  R  R  A
4                              110                              120

1       660       670       680       690       700       710
2    GACGCCGGCGAGTACCGCGCCGCGGTGCACCTCAGGGACCGCGCCCTCTCCTGCCGCCTC
3     D  A  G  E  Y  R  A  A  V  H  L  R  D  R  A  L  S  C  R  L
4                              130                              140

1       720       730       740
2    CGTCTGCGCCTGGGCCAGGCCTCGATG
3     R  L  R  L  G  Q  A  S  M
4                            149
```

FIG.2

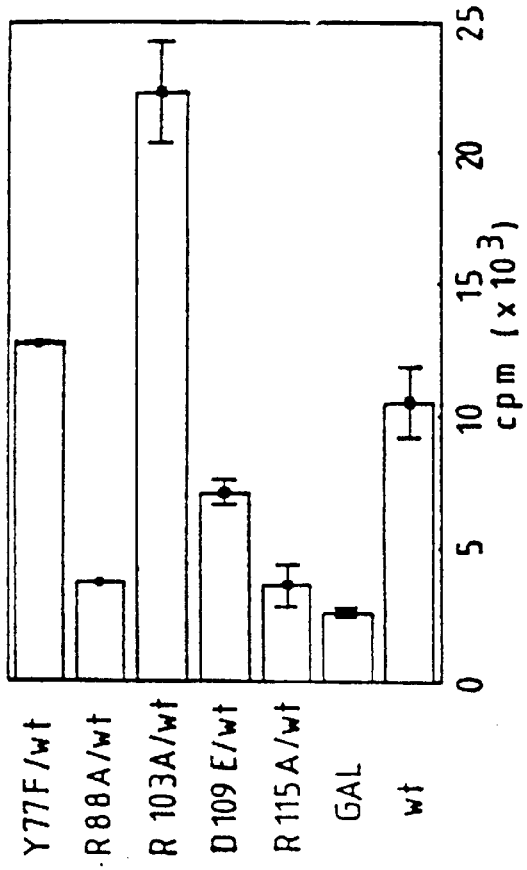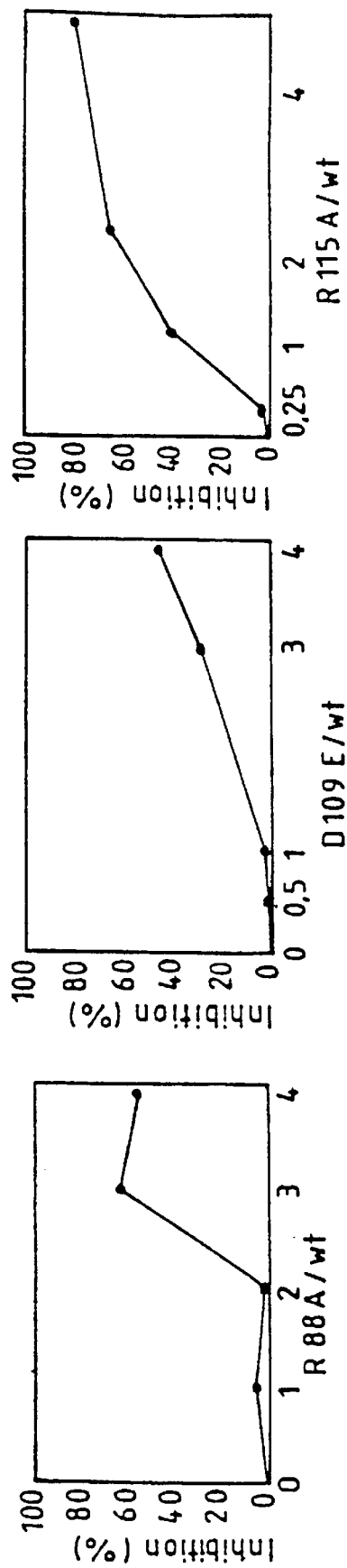
FIG. 8

MUTANTS OF THE LAG-3 PROTEINS AND NUCLEOTIDES ENCODING LAG-3 MUTANTS

CROSS REFERENCE TO RELATED APPLICATION

The present application is the national stage under 35 U.S.C. 371 of PCT/FR97/02126, filed Nov. 25, 1997.

The invention relates to new polypeptides corresponding to mutant forms of the soluble LAG-3 protein or of its fragments.

The lymphocyte activation gene 3 (LAG-3) expressed in activated T cells and human NK cells encodes a type I membrane protein of 498 amino acids with four extracellular domains of the immunoglobulin superfamily (IgSF) (1). The analysis of its sequence has revealed numerous identities with series of amino acid sequences present at corresponding positions on the CD4 receptor, although the overall sequence homology between these two molecules is barely above a base level (approximately 20% sequence identity). Internal sequence homologies also exist in the LAG-3 molecule, between domains 1 (D1) and 3 (D3) as well as between domains 2 (D2) and 4 (D4), which suggests that LAG-3 has evolved, like CD4, through a gene duplication from a pre-existing structure composed of two IgSFs (1). LAG-3 and CD4 can therefore be considered as "first cousins" in the evolution within the IgSF family (2).

The authors of the present invention have shown in previous studies, using a quantitative test of cell adhesion, that the formation of rosettes between COS-7 cells transfected with LAG-3 and B lymphocytes expressing the major histocompatibility complex class II (MHC) molecules is specifically dependent on the interaction between LAG-3 and the MHC class II molecules (2). A direct and specific binding of LAG-3 to various human class II molecules (including various alleles and isotypes) as well as to murine and monkey class II molecules has also been observed with a LAG-3Ig fusion protein (3). This dimeric recombinant globulin LAG-3Ig binds to the monomorphic residue of the MHC class II molecules with a greater affinity (Kd=60 nM at 37° C.) than CD4-Ig (4); LAG-3Ig is in fact capable of blocking the class II molecule/CD4 interaction in a test of intracellular adhesion (4).

The role of the LAG-3/class II molecule interaction was studied using monoclonal antibodies specific for LAG-3 (5) and LAG-3Ig molecules (6). This interaction leads to a negative regulation of the activation of T cell clones. The production of a LAG-3/class II molecule interaction is induced by contacts between T cells, probably via a negative signal from the class II molecules in the T cell.

In general, LAG-3 is only expressed after lymphocyte activation both in vivo and in vitro (5) and does not therefore play a role in the response inducing phase, unlike CD4. Moreover, blocking experiments with monoclonal antibodies have shown that LAG-3 does not participate in the phase for recognition by restricted CD4 T cell clones by the class II molecules. The functional role of LAG-3 is therefore substantially different from that of the other ligands for the MHC molecules, CD4 and CD8.

In patent application PCT/FR95/00593, the authors of the present invention have shown that some soluble polypeptide fractions of the LAG-3 protein of SEQ ID NO:11 were also capable of binding to the class II molecules. They have also underlined the potential importance of the amino acids of the region between residue 46 and residue 77, and in particular positions 73, 75, 76 and 77.

The authors of the invention have now sought to characterize precisely the region(s) of LAG-3 specifically involved in the binding to the class II molecules, and, to do this, have synthesized several mutated forms of LAG-3 possessing targeted mutations in the first two domains of the extracytoplasmic region of the mature protein, that is to say the protein free of signal peptide, having the N-terminal sequence L-Q-P-G-A-E (residues 1-6 of SEQ ID NO. 2). The D1 domain extends from amino acid No. 1 (L), amino acid No. 149 (M); the D2 domain extends from amino acid No. 150 (T) to 239 (G). Surprisingly, the authors of the invention have shown that the substitution of a single amino acid was able to induce well-known modifications in the affinity of LAG-3 for the class II molecules, either by substantially increasing the binding of LAG-3 to these proteins, or on the contrary by inhibiting it partially or totally.

One aspect of the present invention is therefore to provide a purified polypeptide corresponding to a mutated form of the soluble LAG-3 protein or of one of its fragments comprising the extracellular domain D1 and D2 consisting:

either in an amino acid substitution at one of the positions selected from the group consisting of:
position 73 where arginine is replaced by glutamic acid (R73E),
position 75 where arginine is replaced by alanine (R75A) or by glutamic acid (R75E),
position 76 where arginine is replaced by glutamic acid (R76E), or a combination of two or three of the preceding substitutions, or in an amino acid substitution at one of the positions selected from the group consisting of:
position 30 where aspartic acid is replaced by alanine (D30A),
position 56 where histidine is replaced by alanine (H56A),
position 77 where tyrosine is replaced by phenylalanine (Y77F),
position 88 where arginine is replaced by alanine (R88A),
position 103 where arginine is replaced by alanine (R103A),
position 109 where aspartic acid is replaced by glutamic acid (D109E),
position 115 where arginine is replaced by alanine (R115A);

or a deletion of the region between position 54 (P) and position 66 (A).

An other aspect is also the use of these mutants of soluble LAG-3 for the manufacture of medicaments, in particular medicaments which are peptidomimetic for the LAG-3 molecule, that is to say which bind in a similar manner to the MHC class II molecules and which have the same type of immunosuppressive activity as the LAG-3 molecule.

The invention also relates to pharmaceutical compositions comprising, as active ingredient, one of the mutated forms of the LAG-3 protein defined above.

In the text which follows, the polypeptides defined above will be called "mutants of LAG-3".

This definition applies to the polypeptides corresponding to the mutated forms of the whole soluble LAG-3 protein or of fragments of LAG-3 comprising the extracellular domains Di and D2, in particular the fragment composed of the two domains D1 and D2.

The soluble LAG-3 protein corresponds to the sequence between the first N-terminal residue and residue 412 of the mature protein (free of signal peptide).

According to a first embodiment, the invention relates to purified polypeptide mutants of soluble LAG-3 having an affinity for binding to the MHC class II molecules which is greater than the affinity of the wild-type LAG-3 protein. The mutations induced in these peptides are preferably located at the level of the external loop of LAG-3, which is located between residue 46 and residue 77.

More precisely, the invention relates to a purified polypeptide corresponding to a mutated form of the soluble LAG-3 protein or of one of its fragments comprising the two extracellular domains D1 and D2, consisting in an amino acid substitution at one of the positions selected from the group consisting of:

position 73 where arginine is replaced by glutamic acid (R73E), position 75 where arginine is replaced by alanine (R75A) or by glutamic acid (R75E), position 76 where arginine is replaced by glutamic acid (R76E), or a combination of two or three of the preceding substitutions.

Preferably, the mutants of LAG-3 result from a combination of two or three substitutions selected from the group consisting of:
(R73E+R75A),
(R73E+R76E),
(R75A+R76E),
(R73E+R75A+R76E)

These different mutants will be called hereinafter "positive mutants".

According to another embodiment, the invention provides a purified polypeptide corresponding to a mutated form of the soluble LAG-3 protein or of one of its fragments comprising the extracellular domain D1 and D2, consisting in an amino acid substitution at one of the positions selected from the group consisting of:

position 30 where aspartic acid is replaced by alanine (D30A), position 56 where histidine is replaced by alanine (H56A), position 77 where tyrosine is replaced by phenylalanine (Y77F), position 88 where arginine is replaced by alanine (R88A), position 103 where arginine is replaced by alanine (R103A), position 109 where aspartic acid is replaced by glutamic acid (D109E), position 115 where arginine is replaced by alanine (R115A);

or a deletion of the region between position 54 (P) and position 66 (A).

These mutants will be called hereinafter "negative mutants".

The point mutants of LAG-3 according to the present invention may be obtained by site-directed mutagenesis methods.

The site-directed mutagenesis method, which makes it possible to create at will mutations defined both by their nature and by their position is nowadays well known to persons skilled in the art. Its principle is based on a hybridization of a primer oligonucleotide carrying the desired mutation with a denatured DNA template. After formation of a duplex between the mutated DNA strand produced by extension of the primer and the wild-type DNA strand, successive replication cycles under appropriate conditions make it possible to produce DNA mutated on both strands.

It is possible to consider nowadays that site-directed mutagenesis covers a range of protocols and techniques which persons skilled in the art will be able to select or modify depending on their needs. Briefly, site-directed mutagenesis may be carried out according to three types of approach which, in chronological order, are: the single-stranded technology, the double-stranded technology and the PCR technology; each of these three approaches having several variants which are suited to a greater or lesser degree to the specific objectives and constraints of the experimentalist.

Within the framework of the present invention, the site-directed mutagenesis is carried out on the DNA encoding the soluble LAG-3 protein or one of its fragments. The isolated nucleotide sequences encoding the different mutants of LAG-3, as well as their complementary nucleotide sequences, are another aspect of the invention.

The mutant polypeptides of LAG-3, which result from mutations induced on the LAG-3 gene, are obtained by techniques for producing recombinant products after introducing their coding nucleotide sequence into an appropriate cellular host.

In this case, the nucleotide sequence used is placed under the control of signals allowing its expression in the host selected. The cellular host used may be selected from prokaryotic systems such as bacteria, or eukaryotic systems such as for example yeasts, insect cells, CHO (Chinese hamster ovary cells) or any other advantageously commercially available system. A cellular host preferred for the expression of the polypeptides of the invention consists of the fibroblast line COS-7.

The vector should contain a promoter, signals for initiation and termination of translation, as well as appropriate regions for regulation of transcription. It should be capable of being stably maintained in the cell and may optionally possess particular signals specifying the secretion of the translated protein.

These various control signals are selected as a function of the cellular host used. To this effect, the nucleotide sequences encoding the peptides according to the invention may be inserted into vectors replicating autonomously within the host selected, or integrative vectors for the host selected. Such vectors are prepared according to the methods commonly used by persons skilled in the art, and the clones resulting therefrom may be introduced into an appropriate host by standard methods, such as for example electroporation.

The vectors for expressing the polypeptides of the mutants of LAG-3 which are defined above also form part of the present invention.

In the case of the COS-7 cells, the transfection may be carried out using the vector PCDM8, as described in (2).

The invention relates, in addition, to the cells transfected with these expression vectors. These cells may be obtained by the introduction into host cells of a vector for expressing a mutant of LAG-3 as defined above, followed by the culturing of the said cells under conditions allowing the replication and/or expression of the transfected nucleotide sequence encoding a mutant of LAG-3.

When the mutants of LAG-3 are expressed at the surface of the transfected cells, the latter may be used in cell binding and adhesion tests to study the capacity of these mutants to bind to various ligands, in particular membrane antigens of certain cell populations, in particular the MHC class II molecules.

The host cells can also be used in a method for producing a mutant polypeptide of LAG-3, the method itself being included in the present invention, and being characterized in that the transfected cells are cultured under conditions allowing the expression of a mutant recombinant polypeptide of LAG-3, and in that the said recombinant polypeptide is recovered.

The methods of purification used are known to persons skilled in the art. The recombinant polypeptide may be purified from cell lysates and extracts, from the culture medium supernatant, by methods used individually or in combination, such as fractionation, chromatographic methods, immunoaffinity techniques with the aid of specific mono- or polyclonal antibodies, and the like.

An advantageous variant consists in producing a recombinant mutant of LAG-3 fused with a "carrier" protein, for example an immunoglobulin or an immunoglobulin region, to form a chimeric protein. One of the advantages of this system is that it allows stabilization of and a reduction in proteolysis of the recombinant product and simplification of the purification when the fusion partner possesses affinity for a specific ligand.

Fusion proteins consisting of fragments of the extracytoplasmic domain of LAG-3 which are bound to the joining region —$CH_2$—$CH_3$ of the heavy chain of a human immunoglobulin (Ig) have in particular been described in application PCT/FR95/00593.

Among the mutant peptides of LAG-3 according to the invention, the positive mutants, that is to say those having affinity for the MHC class II molecules which is greater than the wild-type molecule, can be advantageously used for the manufacture of pharmaceutical compositions having an immunomodulatory activity.

Also included in the invention are the said pharmaceutical compositions comprising, as active ingredient, a mutant of LAG-3, combined with a pharmaceutically acceptable vehicle. Such compositions offer a new approach for controlling the immune responses involving a cellular interaction between activated T cells and cells expressing the MHC class II molecules. These compositions are, for example, useful for exerting an immunosuppressive effect in the case of pathologies linked to abnormal or exacerbated immunological reactions such as autoimmune diseases or the rejection of organ transplants.

The pharmaceutical compositions of the invention are also useful for preventing or slowing down tumour growth IN VIVO. Natural T cell immunosuppression within human tumours is now a recognized biological reality. Consequently, small molecules involved in the LAG-3/MHC class II molecule interaction offer a new line of action in anticancer immunotherapy on this type of relationship between a tumour and the host organism.

The therapeutic compositions according to the present invention may be formulated according to the usual techniques. The vehicle may be in a variety of forms depending on the route of administration selected: oral, parenteral, sublingual, rectal or nasal.

In the case of compositions for parenteral administration, the vehicle will generally comprise sterile water as well as other optional ingredients promoting solubility or the preservation property of the composition. The parenteral routes of administration may consist in intravenous, intramuscular or subcutaneous injections.

The therapeutic composition may be of the sustained-release type, in particular for long-term treatments, for example the treatment of autoimmune diseases or for controlling organ transplant rejection. The dose to be administered depends on the subject to be treated, in particular the capacity of their immune system to reach the desired level of protection. The precise quantities of active ingredient to be administered may be determined without difficulty by the practitioner who will initiate the treatment.

The therapeutic compositions according to the invention may comprise, in addition to one or more mutants of LAG-3, another active ingredient, optionally bound by a chemical bond to the mutant of LAG-3. There may be mentioned, by way of example, soluble mutants of LAG-3 according to the invention fused with a toxin: for example ricin or diphtheria toxoid, which are capable of binding to MHC class II molecules and of killing the target cells, for example leukaemia or melanoma cells, or which are fused with a radioisotope.

The use of the negative mutant peptides, that is to say those whose affinity for the MHC class II molecules is totally or partially reduced, illustrates another advantageous aspect of the invention.

The properties of these peptides indeed provide information on the molecular interactions between LAG-3 and the MHC class II molecules, which makes them useful for the manufacture of molecules which are agonists or antagonists for the interaction between LAG-3 and the MHC class II molecules.

As will be illustrated below by the examples, various structures of LAG-3 are probably responsible for the oligomerization and the interaction with the MHC class II molecules. Some negative mutants of LAG-3 may allow oligomerization with the wild-type protein (in soluble form or bound to the membrane), and modify the interaction of the resulting complexes with the MHC class II molecules. Such mutants may thus induce reversion of certain functions of LAG-3. Consequently, it appears that the negative mutants of LAG-3 constitute advantageous tools for developing small-sized agonists or antagonists derived from LAG-3 or the MHC class II molecules.

Other characteristics and advantages of the invention are illustrated by the examples in the remainder of the description, as well as by the figures whose legends are indicated below.

LEGEND TO THE FIGURES

FIG. 1 represents the expression vector pCDM8-LAG-3 and pCDM8-GAL. The fragment FDC containing the gene encoding LAG-3 was introduced into the BstXI site of pCDM8 under the control of the cytomegalovirus promoter (pCDM8-LAG-3C) or in the opposite direction (pCDM8-GAL).

FIG. 2 represents the nucleotide (SEQ ID NO:1) and protein sequences (SEQ ID NO:2) of the first domain D1 of LAG-3. The nucleotide sequence of the domain D1 of LAG-3 is indicated line 2. The nucleotides are positioned (line 1) according to the numbering of the LAG-3 sequences which have been deposited at EMBL (X51984). The protein sequence is given using the one-letter amino acid code (line 3). The position of each amino acid is indicated line 4. The sequence of the N-terminal end (Leu 1) was determined by protein sequencing of the LAG-3 molecule purified—from the membrane of activated human lymphocytes. The position of the primers used to amplify the sequences to be mutagenized is indicated by the arrows. The SfanI and EspI sites, which are used to digest the DNA fragments, are underlined. The codons R73, R75 and R76 are surmounted by asterisks. The DNA fragment of 103 base pairs which was subcloned in order to generate the mutated forms of LAG-3 is indicated in bold characters.

FIG. 3 represents a strategy used to generate the mutated forms of LAG-3. The expression vectors encoding the mutated forms of LAG-3 were obtained by linking three subfragments of pCDM8-LAG-3C and one SfanI-EspI fragment obtained by PCR amplification using primers containing the appropriate point mutations.

FIG. 4. represents the quantitative measurement of the cellular binding between LAG-3 transfectants and B cells expressing MHC class II molecules.

The specific binding of the Daudi cells to the selected LAG-3 transfectants was quantified after radioactive labelling with $^{51}$Cr of the Daudi cells (values obtained in duplicate wells).

The nonspecific binding level is indicated by the binding to the transfectants containing the vector pCDM8 carrying the LAG-3 gene inserted in the opposite orientation (pCDM8-GAL).

FIG. 5 represents a comparison of the binding of the mutants of LAG-3 to the MHC class II molecules compared with that of the wild-type (wt) LAG-3 molecule at different expression levels.

The Cos-7 cells were respectively transfected with GAL (0.3 µg), 0.03, 0.1, 0.3 and 1 µg of DNA of pCDM8 LAG-3 wild-type, (open circle symbol o). The DNA of LAG-3 mutant was used at 0.03 µg per transfection. The expression of LAG-3 is indicated in arbitrary fluorescence unit (FU) using 15A9, and the binding to the class II molecules was determined by counting counts per minute (cpm) in a test of cell adhesion using Daudi cells labelled with $^{51}$Cr.

Figure 1:
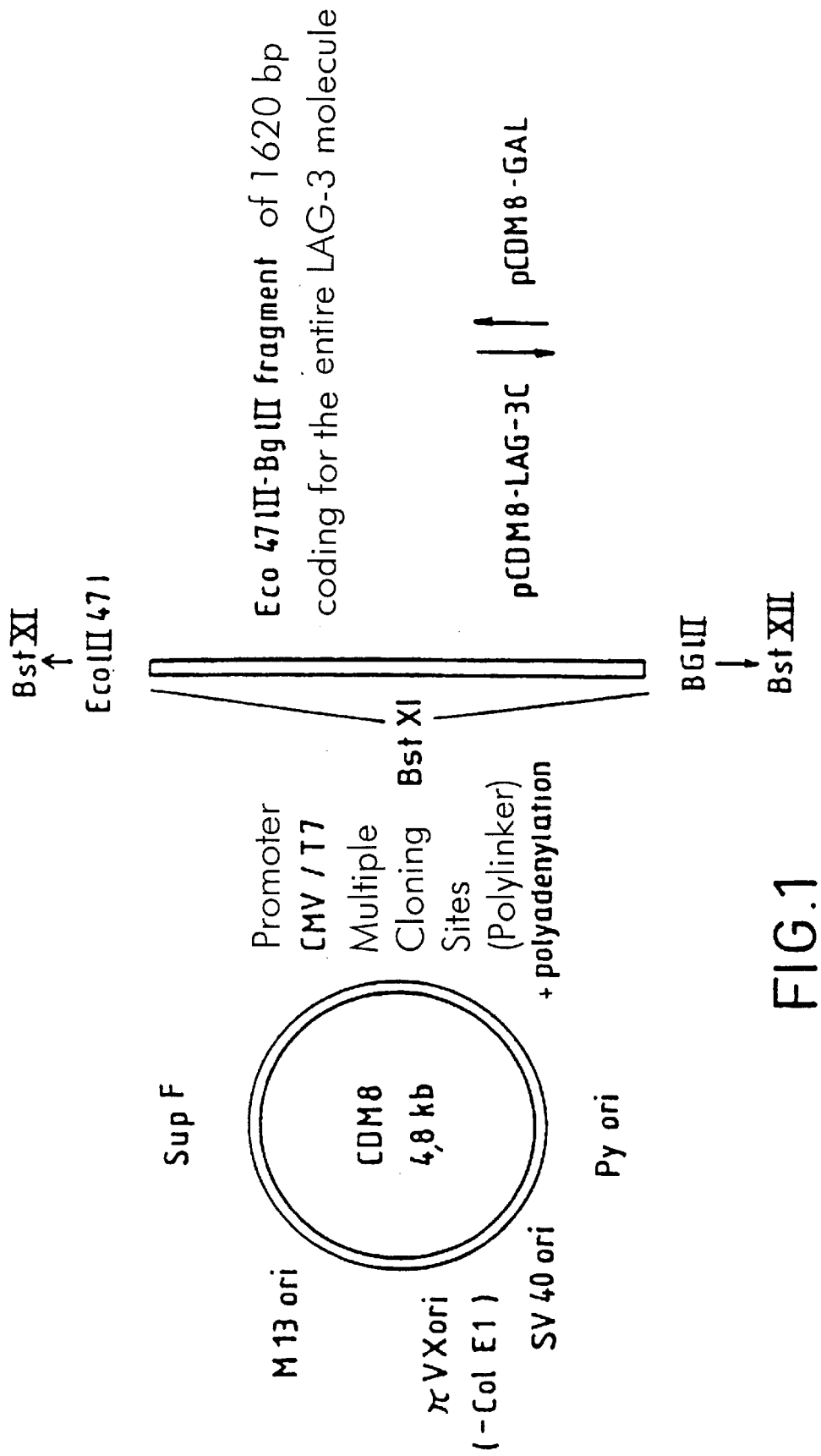

The binding of CD8-Ig, LAG-3Ig (D1D4 or D1D2, 100 nM each) is revealed with F-ITC-labelled goat serum anti-human immunoglobulins. The binding of the monoclonal antibody 9.49 (anti-DR) is revealed with F-ITC-labelled goat serum anti-mouse immunoglobulins. OKT3 (anti-CD3) is a control antibody IgG1 of the same isotype.

FIG. 8 represents an experiment showing the effects of a co-expression of certain negative mutants with wild-type (wt) LAG-3 on the cellular interactions.

A co-expression of the molecules of mutant LAG-3 R88A, D109E and R115A with the wild-type LAG-3 protein inhibits the binding between the transfected Cos cells and the Daudi cells expressing the MHC class II molecules. The quantities of DNA used for the transfection were 10 µg/ml for wild-type (wt) LAG-3 and the negative control (GAL) and 40 µg/ml for the mutants (FIG. 8a). The binding to the class II molecules was determined by counting the counts per minute (cpm) in a test of cell adhesion using Daudi cells labelled with $^{51}$Cr. FIG. 8b shows the inhibition of the binding of the Daudi cells as a function of the quantity of transfected DNA encoding R88A, D109E or R115A. The DNA of wt LAG-3 (10 µg/ml) was mixed with varying quantities of DNA of the mutant molecules (mutant DNA/wild-type DNA indicated on the x-axis) and DNA of pCDM8 was added in order to maintain the total quantity of transfected DNA at 50 µg/ml.

MATERIALS AND METHODS

Monoclonal Antibodies and Fusion Proteins

The monoclonal antibodies anti-LAG-3, 17B4, 4F4 (specific for the LAG-3.1 epitope), 11E3 (LAG-3.2) and 15A9 (LAG3.3) (2), (5) have been previously described. The dimers LAG-3IgD1D4 and LAG-3IgD1D2 were prepared as described previously (3). Conditioned media of Cos-7 cells were used as source of immunoglobulin (Ig) fusion proteins. The supernatants are purified on ConA immunoaffinity column (binding the Fe region of human Ig's).

Vectors for Expressing the Mutants of LAG-3 and Adhesion Tests

The plasmid pCD8 is an expression vector developed by Seed (1987) which allows the cloning of cDNA and their expression either by bacteria or by eukaryotic cells. It contains a ColE1 and SUP F (tRNA suppressor) sequence allowing the expression of resistance to tetracyclin and to ampicilin in bacteria containing an episome P3 (Kan$^R$ amber tet$^R$, ambrer amp$^R$). This episome confers on the bacterial strains resistance to kanamycin. pCDM8 is composed of a multiple cloning site (polylinker) of 358 base pairs (bp), enhancer sequences of cytomegalovirus (CMV) and a replication origin of the SV40 virus and the Polyomavirus. The deletion of 800 base pairs from pCDM8 containing the replication origin of the Polyomavirus made it possible to generate the plasmid pCDM7.

The selection of the primers was carried out with the aid of a computer search ("PC/GENE" environment) on standard selection criteria such as: size of the primer, Tm (melting temperature), richness in GC, absence of vague homology.

The reaction mixtures, including the plasmid sequences of pCDM8 or pCDM7, were used to transform Escherichia coli bacteria strain MC1061/P3. This bacterial strain possesses the episome P3 of 60 base pairs in a small number of copies, which codes for a natural resistance to kanamycin and for an inducible "amber" type gene, for ampicillin and for tetracyclin. To avoid spontaneous reversions, the selection of the colonies carrying recombinant plasmids was carried out on media containing ampicillin and tetracyclin.

The production of expression vectors was carried out by the culture (250 ml) of transformed bacteria followed by extraction of the DNA with a Maxiprep "QIAGEN" kit (Chatsworth, Calif.).

The mutants of LAG-3 possessing a targeted mutation were prepared from oligonucleotide primers covering the sequence comprising the site for the desired mutation. The products were obtained by PCR (14) or by insertion of a mutated synthetic double-stranded oligonucleotide. The sequencing of the PCR products was carried out with the Sequenase kit according to the manufacturer's recommendations (United State Biochemical Corp., Cleveland, Ohio).

The Cos cells were cultured in RPMI 1640 supplemented with 10% foetal calf serum (FCS). The Cos-7 cells were transfected with the plasmid pCDM8-LAG-3C (2) by electroporation using a Cellject apparatus (Eurogentec, Liège, Belgium). The electroporation was carried out in 500 µl at 200 v, 1500 µF and 30 µg/ml of plasmid in a culture medium containing 5×10$^6$ cells/ml. Briefly, 2×10$^8$ B cells were incubated for 45 minutes at 37° C. with 2 mCi of $^{51}$Cr (final volume=3 ml). The cells were washed three times and then used for the binding experiments. Two days after the transfection, the Cos cells were treated with 1 mM EDTA 1X PBS and redeposited on plates at 0.05×10$^6$ cells/well in flat-bottomed 12-well tissue culture plates. 24 hours later, 5.5×10$^6$ Daudi B cells labelled with $^{51}$Cr were incubated in duplicate in wells on these monolayers of Cos cells (final volume=550 µl) for one hour. The Daudi cells were then aspirated and the wells were washed five to seven times by gently adding 1 ml of medium dropwise. The summits of the wells were washed by aspiration with a Pasteur pipette. The remaining cells were lysed in 1 ml of PBS, 1% Triton for 15 minutes at 37° C. The lysates were then centrifuged at 10,000 revolutions/min for 10 minutes and the radioactivity was counted on 500 μl of the resulting supernatant. The number of rosettes (more than 5 Daudi cells) obtained with the LAG-3 mutants was determined relative to the number of rosettes obtained with Cos-7 cells transfected with wild-type LAG-3. The Cos-7 cells transfected with the vector pCDM8 containing the LAG-3 insert in the opposite orientation (GAL) served as negative control for the enumeration of the formation of rosettes.

Immunofluorescence and Flow Cytometry Labelling of the Transfected Cells

The level of expression of mutant LAG-3 was studied with the reactivity of the antibody 15A9 because the epitope recognized by it (LAG-3.3) was never affected by the mutations. The level of expression was calculated by means of arbitrary fluorescence units (FU) defined by the following formula:

FU=% of positive cells×mean fluorescence of positive cells

To compare the level of expression of LAG-3 between the mutants and the wild-type (or wt) protein, the relative levels of expression were calculated as indicated below, using the monoclonal antibody 15A9 and a control monoclonal antibody (called "neg"):

$(FU_{15A9}\text{mutant} - FU_{neg}\text{mutant})/(FU_{15A9}\text{mutant}) - FU_{neg}\text{wt})$ The reactivity of the monoclonal antibody towards the mutated LAG-3 molecules was calculated as follows:

$$\frac{(FU_{mAb}\text{mutant} - FU_{neg}\text{mutant})/(FU_{15A9}\text{mutant}) - FU_{neg}\text{mutant})}{(FU_{mAb}\text{wt} - FU_{neg}\text{wt})/(FU_{15A9}\text{wt}) - FU_{neg}\text{wt})}$$

Production and Purification of LAG-3D1D2Ig and LAG-3D1D4Iq

The Cos cells were cultured in RPMI-1640 medium supplemented with 10% foetal calf serum (FCS). About $10^7$ Cos cells were transfected with 50 μg either of pCMD7-LAG-3D1D2Ig or of pCDM7-LAG-3D1D4Ig by electroporation using a Cellject apparatus (Eurogentec, Liège, Belgium).

The transfected cells were inoculated on Petri dishes with RPMI medium containing 5% of FCS at a density of $2.5×10^5$ cells per ml. Twelve hours later, the culture medium was removed and replaced with FCS-free RPMI medium. The culture supernatants were harvested and again replaced with fresh FCS-free RPMI medium on days 3, 6, 9 and 12 after transfection. The culture supernatants were then centrifuged at low speed in order to remove the cellular debris, and then clarified by centrifugation at 10,000 ×g for 30 minutes and filtered on 0.22μcellulose acetate filters.

The immunoadhesins were then purified by affinity chromatography using a protein A Sepharose column (Pharmacia, Sweden) equilibrated with 0.05 M sodium citrate, pH 8. After adsorption of the immunoadhesins, the column was washed with 0.05 M sodium citrate buffer, pH 8, and the proteins specifically retained by the column were eluted with a 0.05 M sodium citrate buffer pH 3. To avoid degradation of the immunoadhesins, all the fractions were neutralized with 2 M Tris-HCl, pH 8, and then dialysed against RPMI medium. Analysis by SDS-PAGE followed by silver nitrate staining made it possible to determine that the immunoadhesins were purified to homogeneity. After ultrafiltration on polyestersulphone membranes (Filtron, Northborough, Mass.), it was possible to carry out directly the analysis of the binding of these immunoadhesins on MHC class II positive Daudi cells by immunofluorescence.

EXAMPLES

I—Construction of the LAG-3 Mutants: R73E, R75A, R75E and R76E

The Eco47III-BgIII fragment of 1620 base pairs called FDC (Triebel et al., 1990) encoding the whole LAG-3 molecule was introduced after addition of BstXI binding segments (linkers) (Invitrogen, San Diego, Calif.) into the expression vector pCDM8 itself linearized by digestion with the enzyme BstXI (FIG. 1). The plasmids containing the LAG-3 gene under the control of the cytomegalovirus promoter or the LAG-3 gene in the opposite orientation were selected and called pCDM8-LAG-3c and pCDM8-GAL, respectively.

Figure 3:
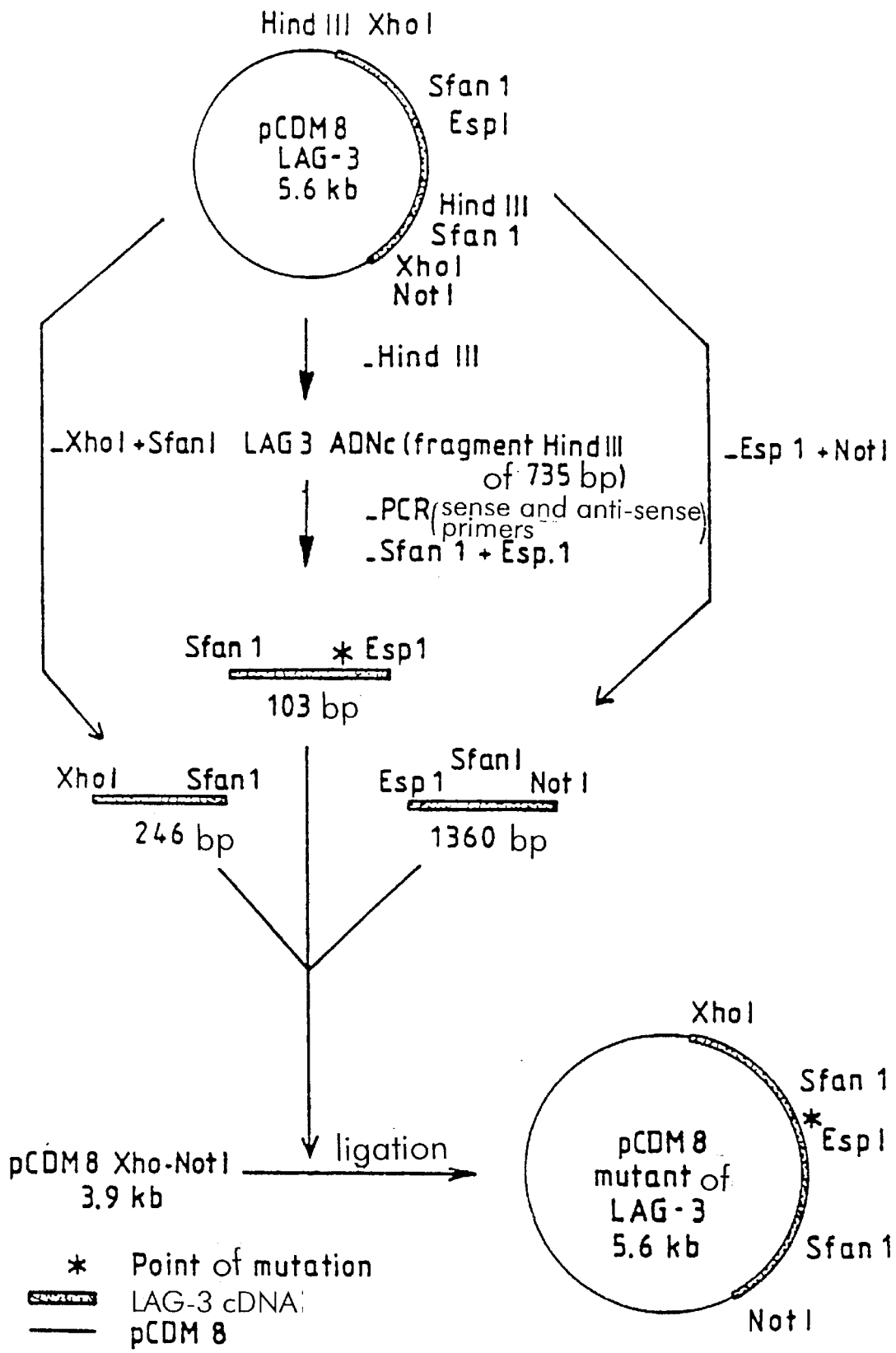

The DNA fragments carrying point mutations at the codons of amino acids 73, 75 and 76 were obtained by PCR amplification using the primer called OU (coding strand) in Table 1 and one of the primers called R73E, R75A, R75E or R76E (complementary strand) in Table 1. The DNA fragments containing the desired mutation was then digested with the restriction enzymes EspI and SfanI and the various mutated EspI-SfanI fragments of 103 base pairs (FIGS. 2 and 3) were purified after agarose gel electrophoresis.

In parallel, pCDM8-LAG-3 was digested either with XhoI and SfanI or with EspI and NotI. The XhoI-SfanI fragment of 246 base pairs containing the 5' part of the LAG-3 cDNA, the EspI-XhoI fragment of 1362 base pairs containing the 3' part of the LAG-3 cDNA and the XhoI-NotI fragment of 3900 base pairs containing pCDM7 were purified and linked with one of the four mutated EspI-SfanI fragments of 103 base pairs.

The plasmids carrying the sequences of each mutated form were selected. Nucleotide sequencing of the PCR-amplified sequences of each mutated form confirmed the presence of the point mutations in the codons of amino acids 73, 75 and 76.

TABLE 1

| Primers | Sequences | |
|---|---|---|
| Primer OU | 5' GCC TCC TGG GAA GAG CAG GGG T 3' | (SEQ ID NO:3) |
| Position | 82  81  80  79  78  77  76  75  74  73  72  71  70 | |
| LAG-3 sequence | Val Ser Leu Val Thr Tyr Arg Arg Pro Arg Pro Gly Trp | (residues 70–82 of SEQ ID:2) |
| Coding strand | 3' GTG CGA GTC GTG GCA CAT CGC CGC CCC GGA CCC GGG GGT 5' | (positions 208–246 of SEQ ID NO:1) |
| Complementary strand | 5' CAC GCT CAG CAC CGT GTA GCG GCG GGG CCT GGG CCC CCA 3' | (SEQ ID NO:12) |
| |                                                                                  Glu | |
| | 3'                                                                                  GAG                       5' | |

TABLE 1-continued

| Primers | Sequences | |
|---|---|---|
| Primer R73E | 5' C CAC GCT CAG CAC CGT GTA GCG GCG GGG CTC GGG CCC CCA 3'<br>                                              Ala<br>3'                                         CCG                   5' | (SEQ ID NO:4) |
| Primer R75A | 5' C CAG GCT CAG CAC CGT GTA GCG GGC GGG CCT 3'<br>                                              Glu<br>3'                                        AAG            5' | (SEQ ID NO:5) |
| Primer R75E | 5' C CAC GCT CAG CAC GGT GTA GCG TTC GGG CCT 3'<br>                                              Glu<br>3' 3'                                     AAG           5' | (SEQ ID NO:6) |
| Primer R76E | 5' C CAC GCT CAG CAC CGT GTA TTC GCG GGG CCT 3' | (SEQ ID NO:7) |

Table 1 represents a 5'→3' nucleotide sequence of the primers used to introduce point mutations at codons 73, 75 and 76.

The mutated codons are underlined. The sequences of the codons on the complementary strand (3'→5' direction) and the new amino acids resulting from these modifications are indicated.

The amino acid sequence of the natural sequence of LAG-3 and their respective position are indicated by way of reference.

Similar approaches well known to persons skilled in the art were used to generate the other mutated forms of LAG-3 in Table 2.

II–Analysis of the LAG-3 Mutants in a Test of Cellular Adhesion

The residues referred to are numbered according to the N-terminal sequence of the mature protein. The substitutions indicated were carried out so as to cover the regions such as the external loop, the CDR1, 2 and 3 domain. Single amino acid substitutions were carried out in the LAG-3 molecule (except as regards the double mutant D133A/R134A and the deletion mutant for the external loop 54/66) by site-directed mutagenesis. In general, the substituted amino acid was replaced by alanine. Other substitutions were carried out so as to preserve or modify the hydrophobicity, the hydrogen binding function or the charge.

The mutants obtained were analysed in a test of cellular adhesion. In this system, the mutant and wild-type forms of LAG-3 are expressed in Cos-7 monkey cells transformed with the simian virus SV40 and are tested for their capacity to bind to Daudi cells expressing the class II molecules (2). Since the level of expression at the cell surface varied from one experiment to another with this test, the expression of each mutant was determined and compared with the expression of wild-type LAG-3 in each of the experiments. In most cases, the expression at the surface and the structural integrity of each mutant protein was confirmed by fluorescence analysis of activated cells (FACS) using the monoclonal antibodies 17B4, 11E3 and 15A9 (Table 2). In reality, most of the mutations produced no effect at the level of the binding of the monoclonal antibody. The deletion of the tip of the external loop (54/66) partially or completely destroyed the LAG-3.2 (11E3) and LAG-3.1 (17B4) epitopes respectively. The last epitopes are in part formed by residues R73 and H56 respectively as demonstrated by the lack of reactivity of LAG-3 point mutants R73E, H56F and H56A with the corresponding monoclonal antibody. Given that the reduction or the loss of binding of the antibody is limited to a single monoclonal antibody, this effect was interpreted as being a direct consequence of the mutation in a residue exposed or otherwise as the result of a major structural alteration in the molecule.

Figure 4:
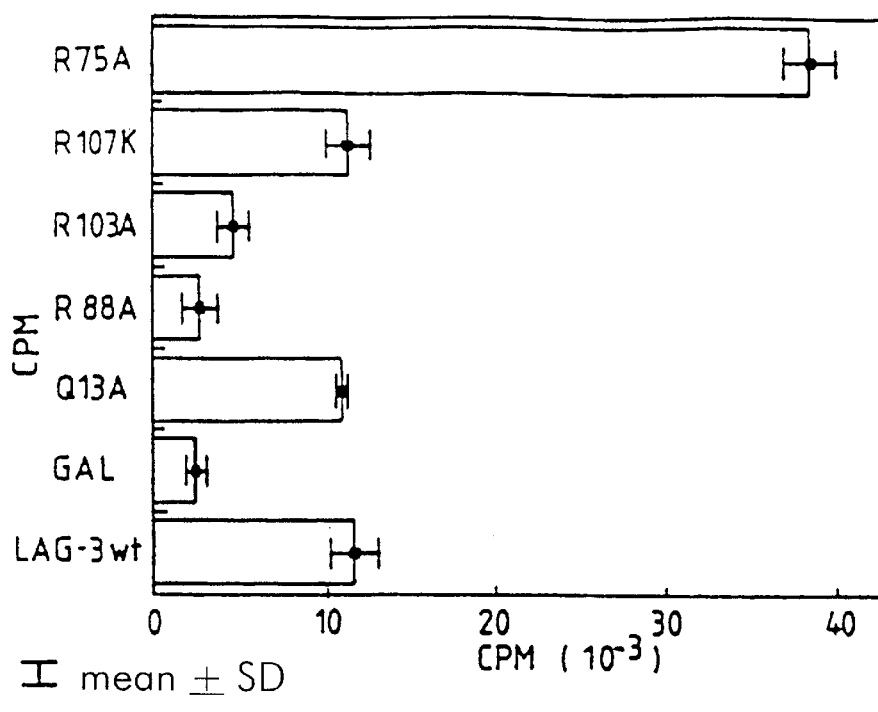

The capacity of each LAG-3 mutant to bind to the class II$^+$Daudi cells was determined in a quantitative test of cellular adhesion (see Table 2). After addition of the Daudi cells to the Cos cells transfected with wild-type LAG-3, characteristic aggregates were formed (2) and the formation of rosettes was analysed under a microscope. The binding of B cells after transfection of LAG-3 was restricted to the Cos-7/LAG-3$^+$cells exclusively as could be observed after attachment and staining with immunoperoxidase with an anti-LAG-3 monoclonal antibody. Moreover, the level of expression of the mutants of LAG-3 was determined in each experiment by immunofluorescence with the monoclonal antibody 15A9 (the LAG-3.3 epitope was not altered by any mutation). Approximately 50% of the cells transfected with the cDNA of mutant or wild-type LAG-3 expressed the molecule in each individual experiment. In most cases, the molecules of mutant LAG-3 were expressed at levels similar to that of the wild-type molecule and therefore the binding of the Daudi cells to these mutants could be directly compared with the binding to the wild-type LAG-3. The binding of the Daudi cells to the LAG-3 mutants was quantitatively analysed with B lymphocytes labelled with $^{51}$Cr in three independent experiments. The results of one of these experiments are indicated in FIG. 4. The mutants R103A and R88A bind weakly to the Daudi cells. In contrast, the replacement, at position 75, of a positively charged amino acid with alanine (R75A) greatly increases binding.

TABLE 2

Effect of various mutations of LAG-3 on the interaction between LAG-3 and the MHC class II molecules

| Mutation | Location of the residue | Anti-LAG-3 monoclonal antibody | | | Level of expression of LAG-3 | Adhesion |
|---|---|---|---|---|---|---|
| | | 17B4 | 11E3 | 15A9 | | |
| wt (wild-type) | — | + | + | + | 1.0 | 1 |
| GAL | negative control | − | − | − | 0 | 0.09 ± 0.06 |
| Q13A | AB | + | + | + | 1.0 | 0.92 ± 0.06 |

TABLE 2-continued

Effect of various mutations of LAG-3 on the interaction between LAG-3 and the MHC class II molecules

| Mutation | Location of the residue | Anti-LAG-3 monoclonal antibody | | | Level of expression of LAG-3 | Adhesion |
|---|---|---|---|---|---|---|
| | | 17B4 | 11E3 | 15A9 | | |
| D30A | BC | + | + | + | 0.81 | 0.41 ± 0.17 |
| H56A | external loop | − | + | + | 0.7 | 0.45 ± 0.28 |
| H56F | external loop | − | + | + | 0.76 | 0.89 ± 0.36 |
| H63A | external loop | + | + | + | 0.89 | 0.83 ± 0.10 |
| H63F | external loop | + | + | + | 0.95 | 0.91 ± 0.18 |
| R73E | external loop | + | − | + | 1.1 | 3.25 ± 1.00 |
| R75A | external loop | + | + | + | 0.67 | 4.20 ± 0.66 |
| R75E | external loop | + | + | + | 1.4 | 4.10 ± 0.90 |
| R76E | external loop | + | + | + | 0.85 | 2.95 ± 1.00 |
| Y77F | C" | + | + | + | 0.75 | 0.05 ± 0.06 |
| R88A | C" D | + | + | + | 0.82 | 0.18 ± 0.0 |
| R103A | DE | + | + | + | 0.93 | 0.49 ± 0.03 |
| R107K | E | + | + | + | 1.1 | 1.02 ± 0.19 |
| D109E | E | + | + | + | 0.81 | 0.18 ± 0.19 |
| R115A | EF | + | + | + | 0.74 | 0.23 ± 0.05 |
| D133A/R134A | FG | + | + | + | 0.99 | 0.78 ± 0.24 |
| D225L | FG (D2) | + | + | + | 0.85 | 0.89 ± 0.13 |
| (D2) | deletion of D2 | + | + | + | 0.6 | 0.11 ± 0.09 |
| (54/66) | deletion of the [lacuna] | − | + | + | 0.6 | 0.08 ± 0.12 |

Table 2 indicates the level of binding of Daudi B cells labelled with $^{51}$Cr or to Cos-7 cells expressing mutants of LAG-3. All the mutations were induced in domain 1, except as regards D225L. The non-specific binding to transfected control cells was not subtracted from the experimental mean cpm values and the results expressed relative to those obtained with wild-type LAG-3 should therefore be compared with the background noise defined by the control cells transfected with GAL (insert of LAG-3 cloned in the opposite orientation into pCDM8). The level of expression of the mutants of LAG-3 was compared with that of wild-type LAG-3. It was studied by measuring the reactivity of the monoclonal antibody 15A9. The relative reactivity of the monoclonal antibody was determined as follows:+: 1–0.6;+/−: 0.2–0.6;−0–0.2.

III—Reduction in the Binding to the Class II Molecules is not the Result of a Reduced Surface Expression of the LAG-3 Mutants.

The molecules of LAG-3 mutants for which the levels of expression were similar to that of wild-type LAG-3 were tested as to their capacity to bind to the Daudi cells expressing the class II molecules. The formation of rosettes and the counts per minute were evaluated and compared with the values obtained with wild-type LAG-3. However, the mutants D30A, H56A, Y77F and R115A and the deletion mutants (D2) and (54/66) were expressed at lower levels than the wild-type LAG-3 molecule. These were therefore re-examined in experiments which made it possible to eliminate the possibility according to which the effects on the binding to the MHC class II molecules could be due to a difference in the level of expression of the LAG-3 molecules. In these experiments (see for example FIG. 5), the expression of wild-type LAG-3 was modulated using variable quantities of DNA in the transfections, in order to cover the different levels of expression of the LAG-3 mutants. For each of the six mutants mentioned above, the bound cpm values were 40% less than those obtained with the cells expressing wild-type LAG-3 at comparable levels of expression. These raw values should however be compared with the background noise which, in this experiment, was 1048 CPM for the Cos cells transfected with GAL.

Figure 5:
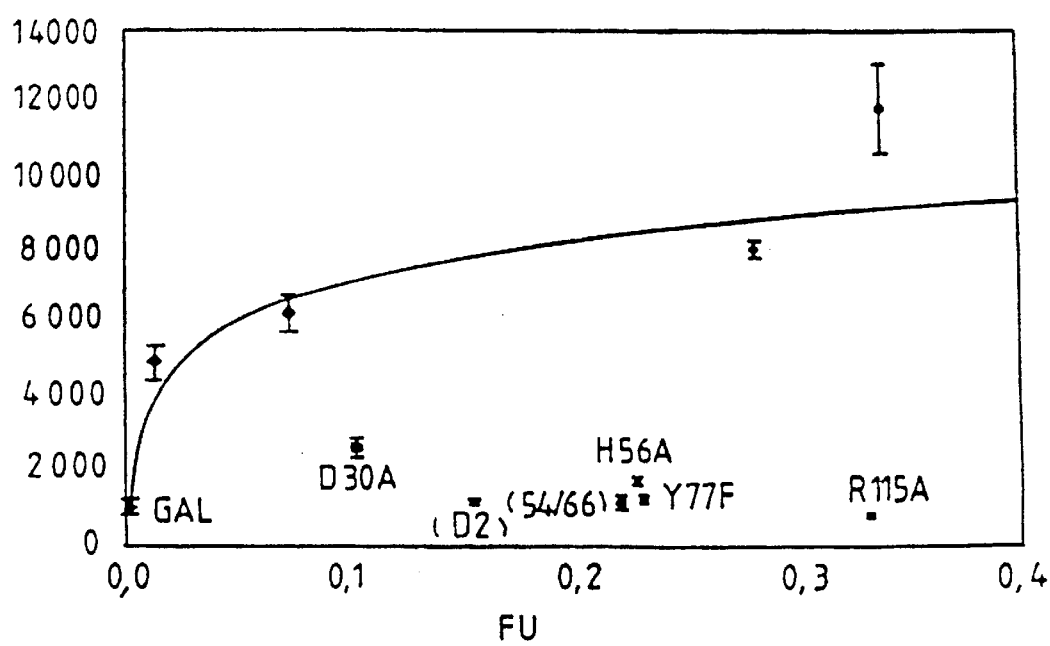

As indicated in FIG. 5, a reduced binding function is therefore the result of an amino acid substitution or of the deletion of a fragment and not the consequence of a reduced surface expression.

IV—Effect of a Change at a Unique Site on the Surface Domains 1 and 2

The effects of mutations in the structure of LAG-3 on its binding to the class II molecules have never been reported previously. Unexpectedly, some mutations were capable of reducing the binding to the class II molecules whereas other mutations increased the affinity of LAG-3 for the class II molecules (Table 2). The mutants Y77F, R88A, D109E and R115A had a greatly inhibited binding whereas those of the mutants D30A, H56A and R103A were only reduced by a factor of 2. In contrast, the mutants R73E, R75A, R75E and R76E had a binding increased by a factor of 3 or more. It will be noted that all these residues are located in the external loop, which suggests an important role of this region in the interactions with the class II molecules.

Another argument in favour of the potential involvement of the external loop of LAG-3 in the binding to the class II molecules is provided by the analysis of the mutant H56A for which the binding is reduced at least two-fold (0.45±0.28 for a GAL negative control of 0.09±0.06) whereas a replacement by a similar amino acid (H56F) does not give rise to an alteration in the binding. The residue H56, which forms part of the epitope 17B4 (see Table 2), is therefore assumed to be in direct contact with the class II molecule. This hypothesis is also supported by the fact that the deletion mutant (54/66)⁻, which lacks the summit of the external loop, does not bind to the class II molecules.

V—A Truncated Form of the Soluble Protein Reveals a Critical Role of Domains 1 and 2 of LAG-3 in the Binding to the MHC Class II Molecules.

To evaluate if the first two domains of LAG-3 contained a site for binding to the class II molecules, the authors synthesized fusion proteins consisting of a human IgG1 Fc fragment and extracellular domains D1 and D2 of LAG-3 (called LAG-3D1D2Ig) or four extracellular domains of LAG-3 (LAG-3D1D4Ig).

Figure 6:
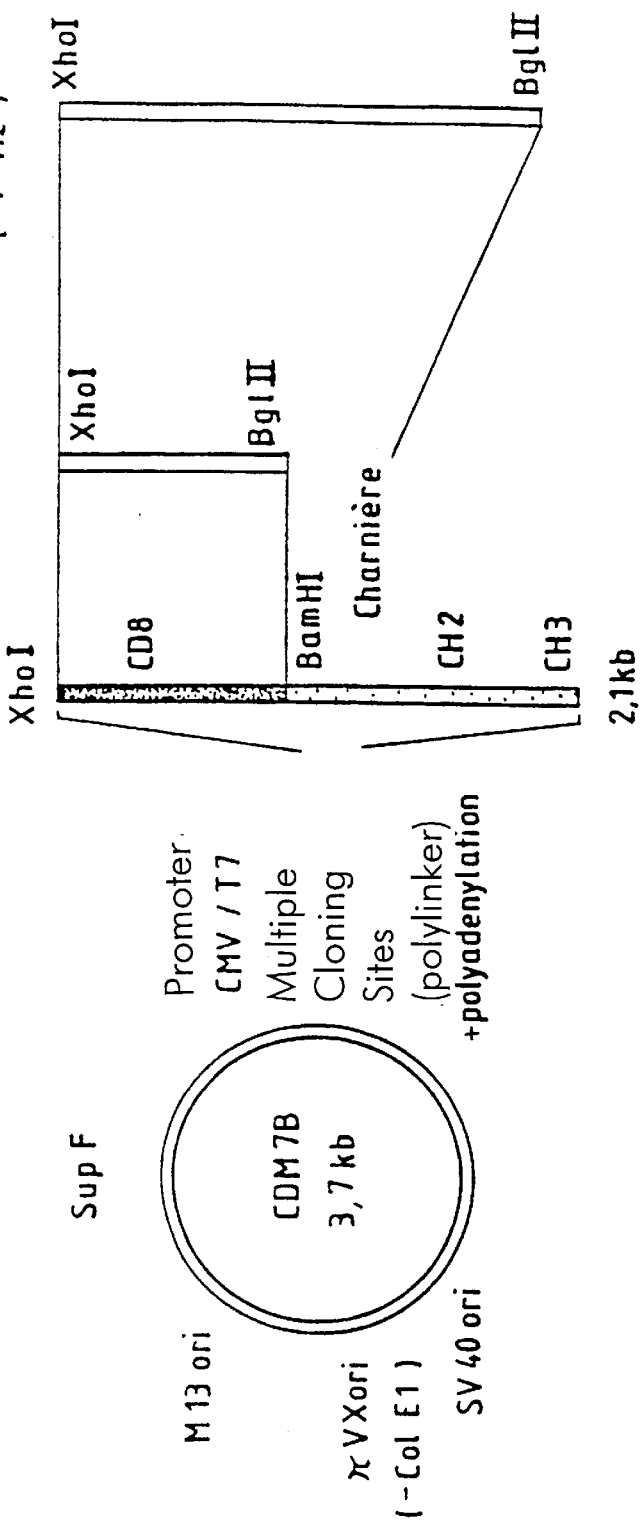
FIG. 6 represents expression vectors encoding LAG-3D1D2Ig and LAG-3D1D4Ig. The DNA fragments encoding either the first 239 or 412 amino acids of LAG-3 were introduced in place of the sequence encoding the extracellular part of CD8 into pCDM7-CD8Ig.

To do this, a DNA fragment of 2.1 kb containing the sequences encoding the extracellular portion of CD8 which were fused with the Fc portion of a human immunoglobulin of isotype IgG1 (that is to say the CH2 and CH3 regions and the hinge region) was introduced into pCDM7 to give the plasmid pCDM7-CD8IgG1 (FIG. 6).

A DNA fragment encoding the extracellular domain of LAG-3 (4 domains) was cloned by the "Hot Start" PCR technique (AmpliWax PCR Gem 100 kit from Perkin Elmer Cetus) using two nucleotide primers containing restriction sites:

1) 5'GCCG<u>CCTCGAG</u>GCCCAGACCATAGGAGAG <u>ATG</u>T3' (SEQ ID NO:8)

comprising the XhoI restriction site (underlined with a dotted line) and a short noncoding 5' sequence followed by the codon for initiation of translation of the LAG-3 gene (underlined with a solid line).
comprising a BglII restriction site (underlined with a dotted line) and the codons for residues 405 to 412 of the LAG-3 molecule.

The DNA fragment thus amplified was digested with the enzymes XhoI and BglII is inserted into pCDM7-CD8-IgG1 itself digested with the enzymes BamHI and XhoI, in place of the sequences encoding the extracellular portion of CD8 (FIG. 6). A chimeric gene consisting of the sequences of the first 412 amino acids of LAG-3 which were fused with the sequences of the Fc portion of a human IgG1 was thus constructed. This chimeric gene is contained in the plasmid called pCDM7LAG-3D1D4Ig under the control of the cytomegalovirus promoter. The sequence of the chimeric gene was checked by nucleotide sequencing.

The DNA fragment encoding the first two domains of LAG-3 was amplified and inserted into pCDM7 CD8-IgG1 as described above, except that the second primer had the sequence:
including a BglII restriction site (underlined with a dotted line) and the codons for amino acids 232 to 239. The plasmid resulting from this recombination, pCDM7-LAG-3D1D2Ig, contains the sequence of LAG-3 encoding the first 239 amino acids which is fused with the sequence encoding the Fc portion of an IgG (FIG. 6).

The fusion molecules LAG-3D1D2Ig and LAG-3D1D4Ig were produced by transient expression in Cos cells and purified by affinity chromatography on a protein A Sepharose column.

Figure 7:
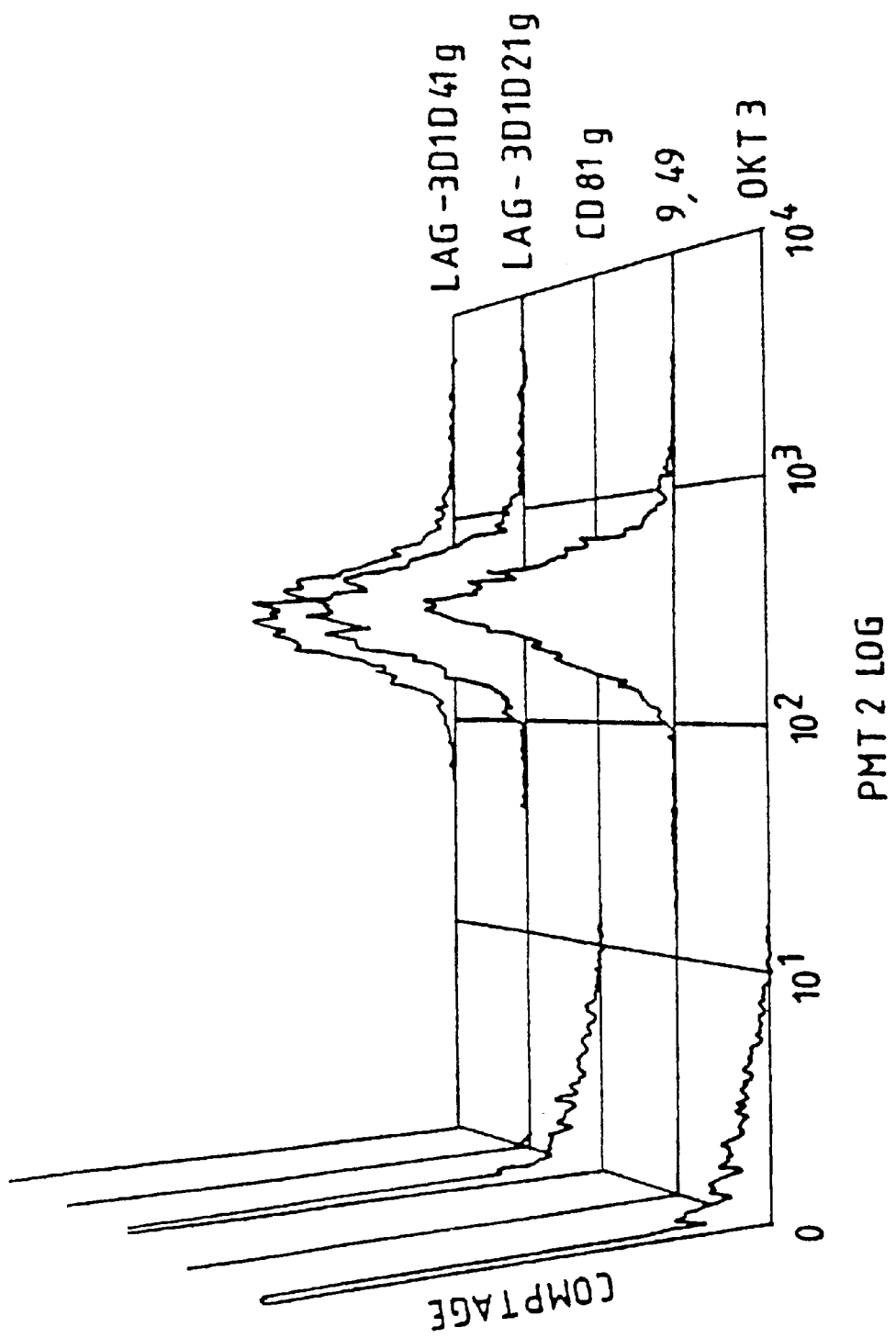
FIG. 7 represents an experiment for the binding of LAG-3 to the Daudi cells expressing the MHC class II molecules.

The binding of LAG-3D1D2Ig to class II$^+$Daudi cells was as intense as that of LAG-3D1D4Ig or of an anti-class II monoclonal antibody (see FIG. 7). Consequently, the structure encoded by exon 2, 3 and 4 ("Ig-like" domains 1+2) is sufficient for the binding to the class II molecules to occur. Furthermore, the deletion of exon 4 ("Ig-like" domain D2) causes inhibition of the formation of rosettes between Daudi cells and Cos-7 transfectants (see Table 1), in spite of a correct surface expression on the Cos-7 cells of the epitopes expressed on D1. These data suggest that the D2 domain is involved either in the LAG-3 class II molecule binding, or in the positioning of D1 during the binding with the class II molecules.

These results also make it possible to conclude that the mutants of LAG-3 according to the invention may advantageously correspond to a mutated form of the truncated form of soluble LAG-3 corresponding to the D1 and D2 domains.

VI—Identification of Two Types of Negative Mutant

In this experiment, the authors of the present invention have shown that three types of negative mutants appear to be involved in the oligomerization of the LAG-3 molecules rather than in the direct interaction with the class II molecules, the final result remaining the same (reduction in the number of rosettes) because the oligomerization of LAG-3 appears to be essential for stabilizing the binding to the MHC class II molecules. In this experiment, the authors of the invention started from the hypothesis according to which oligomerization of the LAG-3 molecules on the cell surface could increase the interaction between LAG-3 and the class II molecules, thus leading to stabilization of the complex. They therefore accepted that if oligomers of LAG-3 were necessary for stabilizing the binding to the class II molecules, certain mutations of LAG-3 each inducing individually a reduction in the binding to the class II molecules could also have an inhibitory effect on the capacity of the molecules of cotransfected wild-type LAG-3 molecules to bind to the class II molecules, given that the wild-type molecule and the mutant molecule would be incorporated into the same oligomers.

The authors of the invention found three dominant negative mutations of LAG-3, R88A, D109E and R115A situated on a lateral face of the molecule (βABED strand) which not only prevent binding to the MHC class II molecules but also inhibit the binding of the wild-type LAG-3 protein to these same molecules (FIG. 8a). This inhibition is dependent on the quantity of transfected mutant LAG-3 DNA (FIG. 8b). Other negative mutations by contrast, namely the Y77F and R103A mutations, affecting residues located on the summit of the D1 domain of LAG-3 did not demonstrate the same inhibitory effect on the binding of the wild-type molecule to the MHC class II molecules (FIG. 8a); and the number of cpm was in fact higher for (Y77F+wt) and (Y103A+wt) than for wt alone, given that these expressed mutant proteins are capable of binding, even weakly, to the MHC class II molecules.

In these transfection experiments, the ratio of mutant DNA to wild-type DNA used was 4/1.

REFERENCES

1. Triebel, F., S. Jitsukawa, E. Baixeras, S. Roman-Roman, C. Genevee, E. Viegas-Pequignot, and T. Hercend. 1990. LAG-3, a novel lymphocyte activation gene closely related to CD4. *J. Exp. Med.* 171:1393.
2. Baixeras, E., B. Huard, C. Miossec, S. Jitsukawa, M. Martin, T. Hercend, C. Auffray, F. Triebel, and D. Piatier-Tonneau. 1992. Characterization of the lymphocyte activation gene 3-encoded protein. A new ligand for human leukocyte antigen class II antigens. *J. Exp. Med.* 176:327.
3. Huard, B., P. Prigent, F. Pages, D. Bruniquel, N. Borie, and F. Triebel. 1995. T cell MHC class II molecules downregulate CD4+T cell response following LAG-3 binding. *Journal of Immunology* (in press).
4. Huard, B., P. Prigent, M. Tournier, D. Bruniquel, and F. Triebel. 1995. CD4/major histocompatibility complex class II Interaction analyzed with CD4- and lymphocyte activation gene-3 (LAG-3)-Ig fusion proteins. *Eur. J. Immunol.* 25:2718.
5. Huard, B., M. Tournier, T. Hercend, F. Triebel, and F. Faure. 1994. Lymphocyte-activation gene 3/major histocompatibility complex class II interaction modulates the antigenic response of CD4+T lymphocytes. *Eur. J. Immunol.* 24:3216.

6. Huard, B., P. Prigent, F. Pages, D. Bruniquel, and F. Triebel. 1996. T cell MHC class II molecules down-regulate CD4+T cell clone response following LAG-3 binding. *European Journal of Immunology* (in press).
7. Gribben, J. G., G. J. Freeman, V. A. Boussiotis, P. Rennert, C. L. Jellis, E. Greenfield, M. Barber, V. A. Restivo, X. Ke, G. S. Gray and L. M. Nadler. 1995. CTLA4 mediates antigen-specific apoptosis of human T cells. *Proc. Natl. Acad. Sci. USA* 92:811.
8. Sun, J., D. J. Leahy, and P. B. Kavathas. 1995. Interaction between CD8 and major histocompatibility complex (MHC) class I mediated by multiple contact surfaces that include the alpha2 and alpha3 domains of MHC class I. *The Journal of Experimental Medicine* 182:1275.
9. Nag, B., H. G. Wada, D. Passmore, B. R. Clark, S. D. Sharma, and H.M. McConnell. 1993. Purified beta-chain of MHC class II binds to CD4 molecules on transfected HeLa cells. *J. Immunol.* 150:1358.
10. Konig, R., X. Shen, and R. N. Germain. 1995. Involvement of both major histocompatibility complex class II alpha and beta chains in CD4 function indicates a role for ordered oligomerization in T cell activation. *The Journal of Experimental Medicine* 182.
11. Giblin, P. A., D. J. Leahy, J. Mennone, and P. B. Kavathas. 1994. The role of charge and multiple faces of the CD8alpha/alpha homodimer in binding to major histocompatibility complex class I molecules: support for a bivalent model. *Proc. Natl. Acad. Sci. USA* 91:1716.
12. Fleury, S., D. Lamarre, S. Meloche, S. E. Ryu, C. Cantin, W. A. Hendrickson, and R. P. Sekaly. 1991. Mutational analysis of the interaction between CD4 and class II MHC: class II antigens contact CD4 on a surface opposite the gp120-binding site. *Cell* 66:1037.
13. Moebius, U., P. Pallai, S. C. Harrison, and E. L. Reinherz. 1993. Delineation of an extended surface contact area on human CD4 involved in class II major histocompatibility complex binding. *Proc. Natl. Acad. Sci. USA* 90:8259.
14. Mikaelian, I., and A. Sergeant. 1992. A general and fast method to generate multiple site directed mutations. *Nucleic Acids Research* 20:376.

What is claimed is:

1. A purified polypeptide which is a mutated form of the soluble LAG-3 protein of residues 1–412 of SEQ ID NO:11 or of a fragment thereof comprising the extracellular domains D1 and D2, wherein said protein or fragment thereof comprises an amino acid substitution at one of the positions in SEQ ID NO:11 selected from the group consisting of:

position 30 where aspartic acid is replaced by alanine (D30A),
   position 56 where histidine is replaced by alanine (H56A),
   position 77 where tyrosine is replaced by phenylalanine (Y77F),
   position 88 where arginine is replaced by alanine (R88A),
   position 103 where arginine is replaced by alanine (R103A),
   position 109 where aspartic acid is replace by glutamic acid (D1 09E),
   position 115 where arginine is replaced by alanine (R115A);

or wherein said protein or fragment thereof comprises a deletion of the region between position 54 (P) and position 66 (A).

2. An isolated nucleotide sequence encoding one of the polypeptides according to claim 1, or a complementary nucleotide sequence thereof.

3. A polypeptide according to claim 1, which is a mutated form of a fragment of LAG-3 composed of two extracellular domains D1 and D2 of soluble LAG-3.

4. A polypeptide according to claim 1, wherein said amino acid substitution is carried out by site-directed mutagenesis of the nucleic acid sequence encoding said soluble LAG-3 protein.

5. A polypeptide according to claim 1, which is a recombinant polypeptide produced in the form of a fusion protein.

6. A polypeptide according to claim 1, which is a recombinant polypeptide produced in the form of a fusion protein wherein the said polypeptide is fused with a region of an immunoglobulin.

* * * * *

SEQUENCE LISTING

<160> NUMBER OF SEQ ID NOS: 12

<210> SEQ ID NO 1
<211> LENGTH: 447
<212> TYPE: DNA
<213> ORGANISM: Homo sapiens
<220> FEATURE:
<221> NAME/KEY: CDS
<222> LOCATION: (1)..(447)
<223> OTHER INFORMATION:

<400> SEQUENCE: 1

```
ctc cag cca ggg gct gag gtc ccg gtg gtg tgg gcc cag gag ggg gct       48
Leu Gln Pro Gly Ala Glu Val Pro Val Val Trp Ala Gln Glu Gly Ala
1               5                   10                  15 cct gcc cag ctc ccc tgc agc ccc aca atc ccc ctc cag gat ctc agc       96
Pro Ala Gln Leu Pro Cys Ser Pro Thr Ile Pro Leu Gln Asp Leu Ser
            20                  25                  30 ctt ctg cga aga gca ggg gtc act tgg cag cat cag cca gac agt ggc      144
Leu Leu Arg Arg Ala Gly Val Thr Trp Gln His Gln Pro Asp Ser Gly
        35                  40                  45 ccg ccc gct gcc gcc ccc ggc cat ccc ctg gcc ccc ggc cct cac ccg      192
Pro Pro Ala Ala Ala Pro Gly His Pro Leu Ala Pro Gly Pro His Pro
    50                  55                  60 gcg gcg ccc tcc tcc tgg ggg ccc agg ccc cgc cgc tac acg gtg ctg      240
Ala Ala Pro Ser Ser Trp Gly Pro Arg Pro Arg Arg Tyr Thr Val Leu
65                  70                  75                  80 agc gtg ggt ccc gga ggc ctg cgc agc ggg agg ctg ccc ctg cag ccc      288
Ser Val Gly Pro Gly Gly Leu Arg Ser Gly Arg Leu Pro Leu Gln Pro
                85                  90                  95 cgc gtc cag ctg gat gag cgc ggc cgg cag cgc ggg gac ttc tcg cta      336
Arg Val Gln Leu Asp Glu Arg Gly Arg Gln Arg Gly Asp Phe Ser Leu
            100                 105                 110 tgg ctg cgc cca gcc cgg cgc gcg gac gcc ggc gag tac cgc gcc gcg      384
Trp Leu Arg Pro Ala Arg Arg Ala Asp Ala Gly Glu Tyr Arg Ala Ala
        115                 120                 125 gtg cac ctc agg gac cgc gcc ctc tcc tgc cgc ctc cgt ctg cgc ctg      432
Val His Leu Arg Asp Arg Ala Leu Ser Cys Arg Leu Arg Leu Arg Leu
    130                 135                 140
```

```
ggc cag gcc tcg atg                                                      447
Gly Gln Ala Ser Met
145

<210> SEQ ID NO 2
<211> LENGTH: 149
<212> TYPE: PRT
<213> ORGANISM: Homo sapiens

<400> SEQUENCE: 2

Leu Gln Pro Gly Ala Glu Val Pro Val Trp Ala Gln Glu Gly Ala
1               5                   10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Ala Ala Pro Gly His Pro Leu Ala Pro Gly Pro His Pro
        50                  55                  60

Ala Ala Pro Ser Ser Trp Gly Pro Arg Pro Arg Arg Tyr Thr Val Leu
65                  70                  75                  80

Ser Val Gly Pro Gly Gly Leu Arg Ser Gly Arg Leu Pro Leu Gln Pro
                85                  90                  95

Arg Val Gln Leu Asp Glu Arg Gly Arg Gln Arg Gly Asp Phe Ser Leu
                100                 105                 110

Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
        130                 135                 140

Gly Gln Ala Ser Met
145

<210> SEQ ID NO 3
<211> LENGTH: 22
<212> TYPE: DNA
<213> ORGANISM: Artificial Sequence
<220> FEATURE:
<223> OTHER INFORMATION: Primer Sequence

<400> SEQUENCE: 3
gcctcctgcg aagagcaggg gt                                                 22

<210> SEQ ID NO 4
<211> LENGTH: 40
<212> TYPE: DNA
<213> ORGANISM: Artificial Sequence
<220> FEATURE:
<223> OTHER INFORMATION: Primer Sequence

<400> SEQUENCE: 4
ccacgctcag caccgtgtag cggcggggct cgggccccca                              40

<210> SEQ ID NO 5
<211> LENGTH: 31
<212> TYPE: DNA
<213> ORGANISM: Artificial Sequence
<220> FEATURE:
<223> OTHER INFORMATION: Primer Sequence

<400> SEQUENCE: 5
ccacgctcag caccgtgtag cgggcgggcc t                                       31
```

-continued

```
<210> SEQ ID NO 6
<211> LENGTH: 31
<212> TYPE: DNA
<213> ORGANISM: Artificial Sequence
<220> FEATURE:
<223> OTHER INFORMATION: Primer Sequence

<400> SEQUENCE: 6
ccacgctcag caccgtgtag cgttcgggcc t                              31

<210> SEQ ID NO 7
<211> LENGTH: 31
<212> TYPE: DNA
<213> ORGANISM: Artificial Sequence
<220> FEATURE:
<223> OTHER INFORMATION: Primer Sequence

<400> SEQUENCE: 7
ccacgctcag caccgtgtat tcccgggcc t                               31

<210> SEQ ID NO 8
<211> LENGTH: 33
<212> TYPE: DNA
<213> ORGANISM: Artificial Sequence
<220> FEATURE:
<223> OTHER INFORMATION: Primer Sequence

<400> SEQUENCE: 8
gccgcctcga ggcccagacc ataggagaga tgt                            33

<210> SEQ ID NO 9
<211> LENGTH: 35
<212> TYPE: DNA
<213> ORGANISM: Artificial Sequence
<220> FEATURE:
<223> OTHER INFORMATION: Primer Sequence

<400> SEQUENCE: 9
gcgccagatc tacctgggct agacagctct gagaa                          35

<210> SEQ ID NO 10
<211> LENGTH: 34
<212> TYPE: DNA
<213> ORGANISM: Artificial Sequence
<220> FEATURE:
<223> OTHER INFORMATION: Primer Sequence

<400> SEQUENCE: 10
gcgcagatct acccagaaca gtgaggttat acat                           34

<210> SEQ ID NO 11
<211> LENGTH: 476
<212> TYPE: PRT
<213> ORGANISM: Homo sapiens

<400> SEQUENCE: 11

Leu Gln Pro Gly Ala Glu Val Pro Val Val Trp Ala Gln Glu Gly Ala
 1               5                  10                  15

Pro Ala Gln Leu Pro Cys Ser Pro Thr Ile Pro Leu Gln Asp Leu Ser
                20                  25                  30

Leu Leu Arg Arg Ala Gly Val Thr Trp Gln His Gln Pro Asp Ser Gly
            35                  40                  45

Pro Pro Ala Ala Ala Pro Gly His Pro Leu Ala Pro Gly Pro His Pro
        50                  55                  60
```

-continued

```
Ala Ala Pro Ser Ser Trp Gly Pro Arg Pro Arg Arg Tyr Thr Val Leu
 65              70                  75                  80

Ser Val Gly Pro Gly Gly Leu Arg Ser Gly Arg Leu Pro Leu Gln Pro
                 85                  90                  95

Arg Val Gln Leu Asp Glu Arg Gly Arg Gln Arg Gly Asp Phe Ser Leu
                100                 105                 110

Trp Leu Arg Pro Ala Arg Arg Ala Asp Ala Gly Glu Tyr Arg Ala Ala
            115                 120                 125

Val His Leu Arg Asp Arg Ala Leu Ser Cys Arg Leu Arg Leu Arg Leu
        130                 135                 140

Gly Gln Ala Ser Met Thr Ala Ser Pro Pro Gly Ser Leu Arg Ala Ser
145                 150                 155                 160

Asp Trp Val Ile Leu Asn Cys Ser Phe Ser Arg Pro Asp Arg Pro Ala
                165                 170                 175

Ser Val His Trp Phe Arg Asn Arg Gly Gln Gly Arg Val Pro Val Arg
                180                 185                 190

Glu Ser Pro His His His Leu Ala Glu Ser Phe Leu Phe Leu Pro Gln
            195                 200                 205

Val Ser Pro Met Asp Ser Gly Pro Trp Gly Cys Ile Leu Thr Tyr Arg
        210                 215                 220

Asp Gly Phe Asn Val Ser Ile Met Tyr Asn Leu Thr Val Leu Gly Leu
225                 230                 235                 240

Glu Pro Pro Thr Pro Leu Thr Val Tyr Ala Gly Ala Gly Ser Arg Val
                245                 250                 255

Gly Leu Pro Cys Arg Leu Pro Ala Gly Val Gly Thr Arg Ser Phe Leu
                260                 265                 270

Thr Ala Lys Trp Thr Pro Pro Gly Gly Pro Asp Leu Leu Val Thr
            275                 280                 285

Gly Asp Asn Gly Asp Phe Thr Leu Arg Leu Glu Asp Val Ser Gln Ala
        290                 295                 300

Gln Ala Gly Thr Tyr Thr Cys His Ile His Leu Gln Glu Gln Gln Leu
305                 310                 315                 320

Asn Ala Thr Val Thr Leu Ala Ile Ile Thr Val Thr Pro Lys Ser Phe
                325                 330                 335

Gly Ser Pro Gly Ser Leu Gly Lys Leu Leu Cys Glu Val Thr Pro Val
                340                 345                 350

Ser Gly Gln Glu Arg Phe Val Trp Ser Ser Leu Asp Thr Pro Ser Gln
            355                 360                 365

Arg Ser Phe Ser Gly Pro Trp Leu Glu Ala Gln Glu Ala Gln Leu Leu
        370                 375                 380

Ser Gln Pro Trp Gln Cys Gln Leu Tyr Gln Gly Glu Arg Leu Leu Gly
385                 390                 395                 400

Ala Ala Val Tyr Phe Thr Glu Leu Ser Ser Pro Gly Ala Gln Arg Ser
                405                 410                 415

Gly Arg Ala Pro Gly Ala Leu Pro Ala Gly His Leu Leu Phe Leu
                420                 425                 430

Thr Leu Gly Val Leu Ser Leu Leu Leu Val Thr Gly Ala Phe Gly
            435                 440                 445

Phe His Leu Trp Arg Arg Gln Trp Arg Pro Arg Phe Ser Ala Leu
        450                 455                 460

Glu Gln Gly Ile His Pro Arg Arg Leu Arg Ala Arg
465                 470                 475
```

```
<210> SEQ ID NO 12
<211> LENGTH: 39
<212> TYPE: DNA
<213> ORGANISM: Artificial Sequence
<220> FEATURE:
<223> OTHER INFORMATION: Synthetic

<400> SEQUENCE: 12
cacgctcagc accgtgtagc ggcggggcct gggccccca                                    39
```